(12) United States Patent
Fujii

(10) Patent No.: US 8,817,303 B2
(45) Date of Patent: Aug. 26, 2014

(54) CONTROL DEVICE, COMPUTER READABLE MEDIUM, AND PRINTING SYSTEM

(75) Inventor: Masaru Fujii, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 157 days.

(21) Appl. No.: 13/364,165

(22) Filed: Feb. 1, 2012

(65) Prior Publication Data

US 2013/0027718 A1     Jan. 31, 2013

(30) Foreign Application Priority Data

Jul. 25, 2011   (JP) ................. 2011-161551

(51) Int. Cl.
*G06F 3/12* (2006.01)
*G06K 15/00* (2006.01)

(52) U.S. Cl.
USPC ......................... 358/1.15; 358/1.14

(58) Field of Classification Search
None
See application file for complete search history.

(56) References Cited

U.S. PATENT DOCUMENTS

| | | | |
|---|---|---|---|
| 2005/0265764 A1* | 12/2005 | Iwai et al. ................. | 399/408 |
| 2007/0291286 A1* | 12/2007 | Utsunomiya et al. ......... | 358/1.8 |
| 2010/0231966 A1* | 9/2010 | Todaka ..................... | 358/1.15 |

FOREIGN PATENT DOCUMENTS

| | | |
|---|---|---|
| JP | 2001-007961 A | 1/2001 |
| JP | 2007-163559 A | 6/2007 |
| JP | 2010-219630 A | 9/2010 |

* cited by examiner

*Primary Examiner* — Dov Popovici
(74) *Attorney, Agent, or Firm* — Sughrue Mion, PLLC

(57) ABSTRACT

A control device includes a generating unit, a specifying unit, a calculating unit, a determining unit, and a controller. The generating unit generates, upon receiving a print instruction, which includes attribute information representing an attribute of a printed material to be created, processing information by using the attribute information and a preset rule. The specifying unit specifies activation periods of activation operations of activating the respective processing devices indicated by the processing information. The calculating unit calculates processing periods of processing operations executed to create the printed material by the respective processing devices indicated by the processing information. The determining unit determines starting times of the activation operations executed by the respective processing devices indicated by the processing information. The controller controls the respective processing devices indicated by the processing information so that the processing devices start the respective activation operations at the starting times determined by the determining unit.

6 Claims, 9 Drawing Sheets

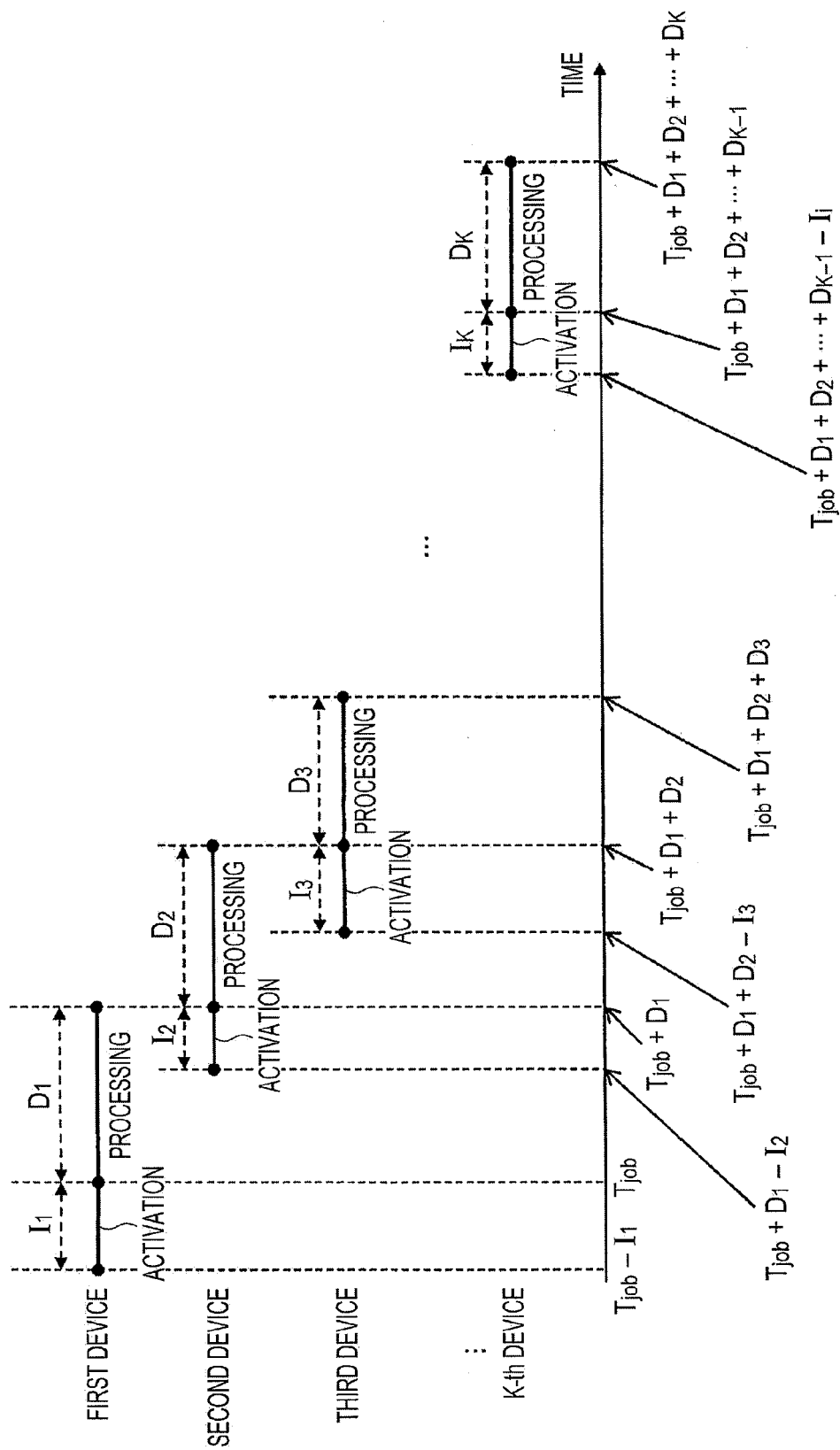

FIG. 4

| DEVICE NUMBER | ACTIVATION STARTING TIME | PROCESSING END TIME |
|---|---|---|
| 1 | $T_{job} - I_1$ | $T_{job} + D_1$ |
| 2 | $(T_{job} + D_1) - I_2$ | $(T_{job} + D_1) + D_2$ |
| 3 | $((T_{job} + D_1) + D_2) - I_3$ | $((T_{job} + D_1) + D_2) + D_3$ |
| ... | ... | ... |
| K − 1 | $T_{job} + \sum_{i=1}^{K-1-1} D_i - I_{K-1}$ | $T_{job} + \sum_{i=1}^{K-1} D_i$ |
| K | $T_{job} + \sum_{i=1}^{K-1} D_i - I_K$ | $T_{job} + \sum_{i=1}^{K} D_i$ |

FIG. 5

| ID | JOB TRANSMISSION TIME ($T_{job}$) | NAME OF DESTINATION DEVICE | IP ADDRESS OF DESTINATION DEVICE |
|---|---|---|---|
| 1001 | 9:47:42 | PREPRESS PROCESSING PC | 192.10.22.101 |

FIG. 6

| ID | ACTIVATION START INSTRUCTION TRANSMISSION TIME | NAME OF TARGET DEVICE | IP ADDRESS OF TARGET DEVICE |
|---|---|---|---|
| 1101 | 9:45:20 | PREPRESS PROCESSING PC | 192.10.22.101 |
| 1102 | 9:48:32 | COLOR LASER PRINTER | 192.10.22.106 |
| 1103 | 10:03:16 | GLUE BINDING MACHINE | 192.10.24.65 |
| 1104 | 10:09:46 | CASE BINDING COVER BINDING MACHINE | 192.10.24.67 |

CONTROL DEVICE, COMPUTER READABLE MEDIUM, AND PRINTING SYSTEM

CROSS-REFERENCE TO RELATED APPLICATIONS

This application is based on and claims priority under 35 USC 119 from Japanese Patent Application No. 2011-161551 filed Jul. 25, 2011.

BACKGROUND (i) Technical Field

The present invention relates to a control device, a computer readable medium, and a printing system.

SUMMARY

According to an aspect of the invention, there is provided a control device including a generating unit, a specifying unit, a calculating unit, a determining unit, and a controller. The generating unit generates, upon receiving a print instruction, which includes attribute information representing an attribute of a printed material to be created, from a terminal device, processing information by using the attribute information included in the print instruction and a rule that is preset regarding an attribute of a printed material and plural processing operations to be executed for creating the printed material having the attribute, the processing information indicating which processing operations are to be executed in which order by which processing devices among plural processing devices that execute different processing operations for creating a printed material, so as to create the printed material to be created. The specifying unit specifies activation periods of activation operations of activating the respective processing devices indicated by the processing information, the activation periods being specified using operation information of the respective processing devices and power state information of the respective processing devices, the operation information and the power state information being obtained from the respective processing devices indicated by the processing information. The calculating unit calculates processing periods of the processing operations executed to create the printed material by the respective processing devices indicated by the processing information, the processing periods being calculated using the operation information, the power state information, and the attribute information included in the print instruction. The determining unit determines starting times of the activation operations executed by the respective processing devices indicated by the processing information by using the activation periods, the processing periods, and the order of the processing operations executed by the processing devices indicated by the processing information, so that an end time of a processing operation executed by a certain processing device among the processing devices matches an end time of an activation operation executed by a next processing device among the processing devices, the next processing device executing a processing operation subsequent to the certain processing device. The controller controls the respective processing devices indicated by the processing information so that the processing devices start the respective activation operations at the starting times determined by the determining unit.

BRIEF DESCRIPTION OF THE DRAWINGS

Exemplary embodiment(s) of the present invention will be described in detail based on the following figures, wherein:

FIG. 3 is a diagram illustrating an example of processing operations executed by individual devices in time series in the case of processing a print job according to an exemplary embodiment of the invention;

FIG. 4 is a diagram illustrating activation starting times and processing end times of the devices illustrated in FIG. 3;

FIG. 5 is a diagram illustrating an example of part of a schedule created by a scheduler;

FIG. 6 is a diagram illustrating an example of part of another schedule created by the scheduler;

DETAILED DESCRIPTION

Figure 1:
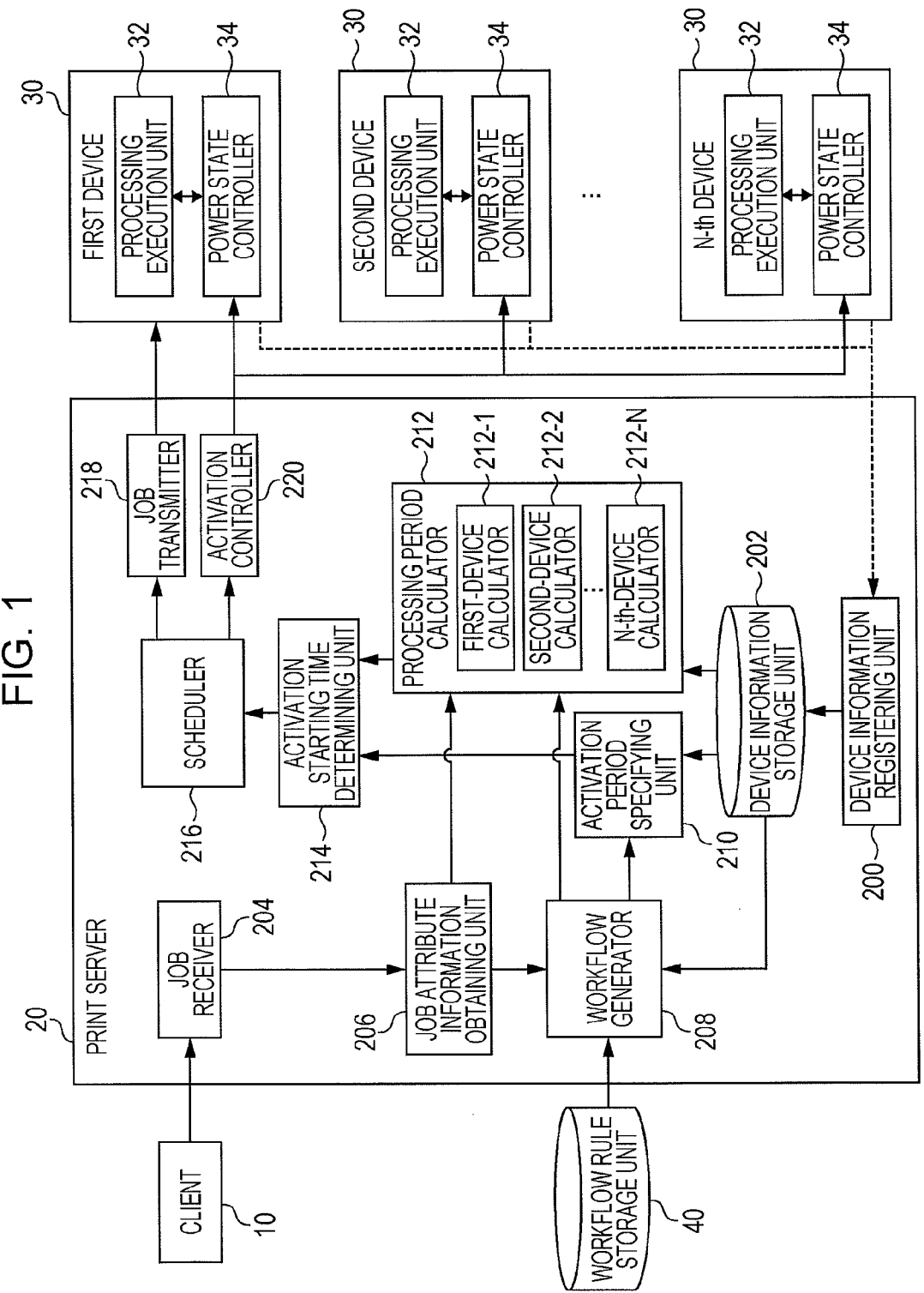
FIG. 1 is a diagram illustrating an exemplary schematic configuration of a system for creating a printed material.

FIG. 1 illustrates an exemplary schematic configuration of a printing system. The printing system illustrated in FIG. 1 includes a client 10, a print server 20, and first to N-th devices 30 (hereinafter simply referred to as devices 30 when they are not distinguished from one another). The client 10 is connected to the print server 20 via a communication medium (not illustrated). The communication medium that connects the client 10 to the print server 20 may be, for example, a network such as a local area network (LAN). The print server 20 is connected to each of the plural devices 30 via communication media (not illustrated). The communication media that connect the print server 20 to each of the devices 30 may be communication media suitable for the respective devices 30. For example, a device 30 that communicates with the print server 20 using a specific type of communication medium may be connected to the print server 20 via the specific type of communication medium. Also, for example, a device 30 that communicates with the print server 20 using a network such as a LAN may be connected to the print server 20 via a network such as a LAN. Additionally, the communication medium that connects the client 10 to the print server 20 and the communication media that connect the print server 20 to the respective devices 30 may be either a wired or wireless communication medium.

The client 10 is a terminal device operated by a user of the system. The client 10 generates, in response to input by the user who provides an instruction to create a printed material, a print job including an instruction to create the printed material, and transmits the generated print job to the print server 20. The client 10 may be realized by a multi-purpose information processing device, such as a personal computer (PC), for example.

The print server 20 controls the individual devices 30 in accordance with a print job received from the client 10, thereby causing the devices 30 to create a printed material. The details of the print server 20 will be described below.

The individual devices 30 perform different parts of processing for creating a printed material. For example, a printer that prints an image onto a medium such as paper, a prepress processor that performs prepress processing before printing is performed by the printer, a postprocessor that performs specific post-processing on a medium on which printing has been performed by the printer, and so forth are provided as the devices 30 in the system. The printer may be a printing device of a known type, such as an inkjet type, a laser type, or a thermal transfer type. The prepress processor may be realized by, for example, installing software that executes prepress processing to a multi-purpose information processing device, such as a PC. The prepress processing is processing for generating data suitable for the characteristics of the printer that is to be used later, and may be, for example, image processing including change of the resolution of image data, color tone correction, and noise reduction. Examples of the postprocessor include a punching device that punches holes in a sheet to be put in a file, a stapler that staples plural sheets together, a folding machine that automatically folds a sheet in a preset folding manner, an insertion machine that automatically inserts a sheet into an envelope, and a binding machine that performs various kinds of binding.

The device 30 serving as a prepress processor is connected to the device 30 serving as a printer via a communication medium that is used for transmitting data resulting from prepress processing to the device 30 serving as a printer. The device 30 serving as a printer may be connected to the device 30 serving as a postprocessor via a physical mechanism for supplying a medium of a printed result to the device 30 serving as a postprocessor (for example, a device that transports a sheet).

The printing system illustrated in FIG. 1 may include, as the devices 30, plural types of prepress processors, printers, and postprocessors. Each of the devices 30 may be an independent device. Alternatively, some or all of the devices 30 may be provided, in a single device, as units that realize the functions of some or all of the devices 30. For example, the devices 30 may be device units constituting an industrial production printer that prints publications or the like.

Each of the devices 30 includes a processing execution unit 32 and a power state controller 34. The processing execution unit 32 executes processing for a function provided in the device 30. For example, in the device 30 serving as a prepress processor, the processing execution unit 32 executes prepress processing. In the device 30 serving as a printer, the processing execution unit 32 executes printing. In the device 30 serving as a postprocessor, the processing execution unit 32 executes any one of the processing operations executed by the above-described postprocessors. The power state controller 34 controls the power state of the device 30. The power state may be an "ON state" in which the device 30 is supplied with power, or an "OFF state" in which the device 30 is not supplied with power. In the exemplary embodiment, the ON state includes three modes: an idle mode; a processing execution mode; and a power-saving mode. In the idle mode, the processing execution unit 32 is in a standby state (idle state) so as to be ready to start processing upon receiving an instruction to start the processing. In the processing execution mode, the processing execution unit 32 of the device 30 executes processing. In the power-saving mode, power is supplied to part of the device 30, and the device 30 is in a standby state in which an amount of power consumed thereby is smaller than that of the device 30 in the idle mode and the processing execution mode. The power-saving mode may include plural modes in accordance with a part of the device 30 to which power is to be supplied.

In the exemplary embodiment, the power state controller 34 has a function of switching the power state in accordance with a control signal received from an external device, such as the print server 20. For example, upon receiving a control signal representing an instruction to specify any one of the above-described power states from the print server 20, the power state controller 34 switches the power state of the device 30 to the power state specified by the instruction represented by the received control signal. Also, for example, the power state controller 34 may switch the power state in accordance with a user's instruction obtained via an input device (not illustrated), such as a power switch, provided in the device 30. Also, for example, the power state controller 34 may switch the power state when a condition preset as a condition for switching the power state is satisfied. For example, the power state may be switched from the idle mode to the power-saving mode at the time when a preset timeout period elapses after an input operation by a user was last received in the idle mode. Alternatively, the power state may be switched from the processing execution mode to any one of the idle mode, the power-saving mode, and the OFF state at the time when the execution of processing in the processing execution mode ends.

Hereinafter, the exemplary embodiment will be described under the assumption that the power state controller 34 of each device 30 switches the power state to the power-saving mode or the OFF state when the execution of processing in the processing execution mode ends.

The print server 20 includes a device information registering unit 200, a device information storage unit 202, a job receiver 204, a job attribute information obtaining unit 206, a workflow generator 208, an activation period specifying unit 210, a processing period calculator 212, an activation starting time determining unit 214, a scheduler 216, a job transmitter 218, and an activation controller 220.

The device information registering unit 200 obtains, from the individual devices 30, operation information about the operations of the individual devices 30 and power state information indicating the current power states of the individual devices 30, and registers the obtained operation information and power state information of the individual devices 30 in the device information storage unit 202. The operation information and power state information of the individual devices 30 are used for processing of the corresponding devices 30 in the activation period specifying unit 210 and the processing period calculator 212, which will be described below.

The operation information of the individual devices 30 obtained by the device information registering unit 200 includes, for example, information indicating the performance of the corresponding devices 30 and information about control of the power state of the corresponding devices 30. The information indicating the performance of a device 30 may be the amount of data or medium that may be processed by the device 30 per unit time, and a time period over which the device 30 performs specific processing. The information about control of the power state of a device 30 may include information about a condition for switching the power state of the device 30 from the idle mode to the power-saving mode. For example, in the device 30 in which the power state is switched from the idle mode to the power-saving mode at the time when a preset timeout period elapses after an input operation by a user was last received in the idle mode, the timeout period may be obtained as part of the operation information. Furthermore, for example, a return period from when the device 30 receives an instruction to return from the OFF state to the idle mode to when switching from the OFF state to the idle mode is performed, and a return period from when the device 30 receives an instruction to return from the power-saving mode to the idle mode to when switching from the power-saving mode to the idle mode is performed may be obtained as part of the operation information. In a case where plural power-saving modes are available in the device 30, the timeout periods and return periods of the respective power-saving modes may be obtained as part of the operation information.

The device 30 serving as a prepress processor may obtain, as operation information, the information indicating the performance of a central processing unit (CPU) of the information processing device that realizes the prepress processor. Also, the device 30 may obtain the timeout period and return period of the prepress processor as operation information.

The device 30 serving as a printer may obtain, for example, operation information including the values of page per minute (PPM) and first print output time (FPOT). Here, PPM represents the number of faces of sheets printed by the printer in one minute. FPOT represents the time period from when a print start instruction is received to when the first printed sheet is output. If the printer is capable of executing both of monochrome printing and color printing, the values of PPM and FPOT for each of monochrome printing and color printing may be obtained as part of the operation information of the printer. Furthermore, if the printer is capable of executing printing using plural document sizes, the values of PPM and FPOT for each document size may be obtained as part of the operation information of the printer. Also, the timeout period and return period of the printer may be obtained as part of the operation information.

The device 30 serving as a postprocessor may obtain different operation information depending on the type of processing performed by the postprocessor. For example, a postprocessor serving as a binding machine may obtain the number of booklets that may be produced in a unit time (for example, one minute). In this binding machine, if the number of booklets that may be produced in a unit time varies in individual ranges of the number of pages included in one booklet, the numbers of booklets that may be produced in a unit time in the individual ranges of the number of pages may be obtained. Also, the timeout period and return period of the postprocessor may be obtained as part of the operation information.

Examples of the operation information of the individual devices 30 obtained by the device information registering unit 200 have been described above. The power state information of the individual devices 30 obtained by the device information registering unit 200 is the information indicating the current power state of the devices 30 among the power states in which the devices 30 may be.

The device information registering unit 200 requests the individual devices 30 to transmit the operation information and power state information so as to obtain the information regularly at preset time intervals. Alternatively, the device information registering unit 200 may obtain the operation information and power state information of the individual devices 30 when the job receiver 204 (described below) receives a print job. The operation information and power state information may be obtained by, for example, using a protocol that is known as a protocol for obtaining information about a device connected via a communication medium. For example, the device information registering unit 200 may obtain the operation information and power state information of each device 30 by accessing management information base (MIB) information of a simple network management protocol (SNMP) for the device 30. Alternatively, for example, the device information registering unit 200 may obtain the operation information and power state information of each device 30 by communicating with the device 30 in accordance with a simple object access protocol (SOAP). Also, a ping command of an Internet protocol (IP) may be used to determine whether the power state is the OFF state or ON state. For example, the device information registering unit 200 transmits a response request based on ping to the individual devices 30, determines the power state of the device 30 that returns a ping response to the request within a preset period to be the ON state, and determines the power state of the device 30 that does not return a ping response within the preset period to be the OFF state.

The device information registering unit 200 registers, in the device information storage unit 202, the obtained operation information and current power state information of the individual devices 30 in association with the identification information of the devices 30.

The device information storage unit 202 is a storage device that stores information about the individual devices 30. The device information storage unit 202 stores, for example, the operation information and current power state information of the individual devices 30 obtained by the device information registering unit 200, in association with the identification information of the individual devices 30. The device information storage unit 202 according to the exemplary embodiment further stores the information indicating the types of the devices 30 in association with the identification information of the individual devices 30. The types of the devices 30 may be a prepress processor, a printer, a postprocessor, and so fourth, as described above. The device information storage unit 202 may further store the specifications of the individual devices 30. For example, in the case of the device 30 serving as a printer, the information indicating the specifications, such as a printing type (inkjet or laser), compatible or incompatible with color printing, and document sizes available for printing, may be stored in association with the identification information of the device 30.

The job receiver 204 receives a print job, which is an instruction to create a printed material, from the client 10. The print job includes attribute information representing the attributes of the printed material to be created. Here, examples of the attributes of the printed material include a document size, simplex/duplex printing, monochrome/color printing, whether or not N-up setting (setting for printing plural pages on one face of a sheet) is performed, the number of pages, the number of copies, and a finishing type. The finishing type corresponds to the processing performed by a postprocessor, and examples thereof include stapling, glue binding, saddle stitch, folding, and insertion into an envelope. The job receiver 204 stores a received print job in a print queue provided in a temporary storage device (not illustrated), and supplies the print job to the job attribute information obtaining unit 206 in a first-in first-out (FIFO) scheme, for example.

The job attribute information obtaining unit 206 obtains the attribute information included in the print job received from the job receiver 204. For example, if attribute information is included as header information of the print job, the job attribute information obtaining unit 206 obtains the attribute information by referring to the header information of the received print job. The job attribute information obtaining unit 206 supplies the obtained attribute information to the workflow generator 208.

The workflow generator 208 generates a workflow for creating a printed material that is to be created in accordance with the print job, by using the attribute information obtained by the job attribute information obtaining unit 206. In the exemplary embodiment, a workflow is the information indicating a processing procedure of creating a target printed material. More specifically, the workflow indicates which processing operations are to be executed by which devices 30 in which order. The workflow generator 208 according to the exemplary embodiment generates a workflow by referring to the content of the workflow rule storage unit 40 that is accessible from the print server 20. A workflow rule according to the exemplary embodiment is a rule for associating a combination of attributes of a printed material with a workflow pattern for creating a printed material having the attributes in the combination. A workflow pattern is the information indicating which types of processing operations are to be executed in which order. The workflow generator 208 according to the exemplary embodiment specifies a workflow pattern corresponding to a combination included in the attributes represented by the attribute information obtained by the job attribute information obtaining unit 206 in accordance with the workflow rule stored in the workflow rule storage unit 40. The workflow generator 208 further specifies the devices 30 corresponding to the types of devices included in the specified workflow pattern among all the devices 30 included in the system. The specification of the devices 30 corresponding to the types of devices included in the workflow pattern may be performed by referring to the identification information and the types of the individual devices 30 stored in the device information storage unit 202. Furthermore, the workflow generator 208 generates a workflow indicating that the processing operations are to be executed by the specified devices 30 in the order indicated by the specified workflow pattern.

Figure 2A:
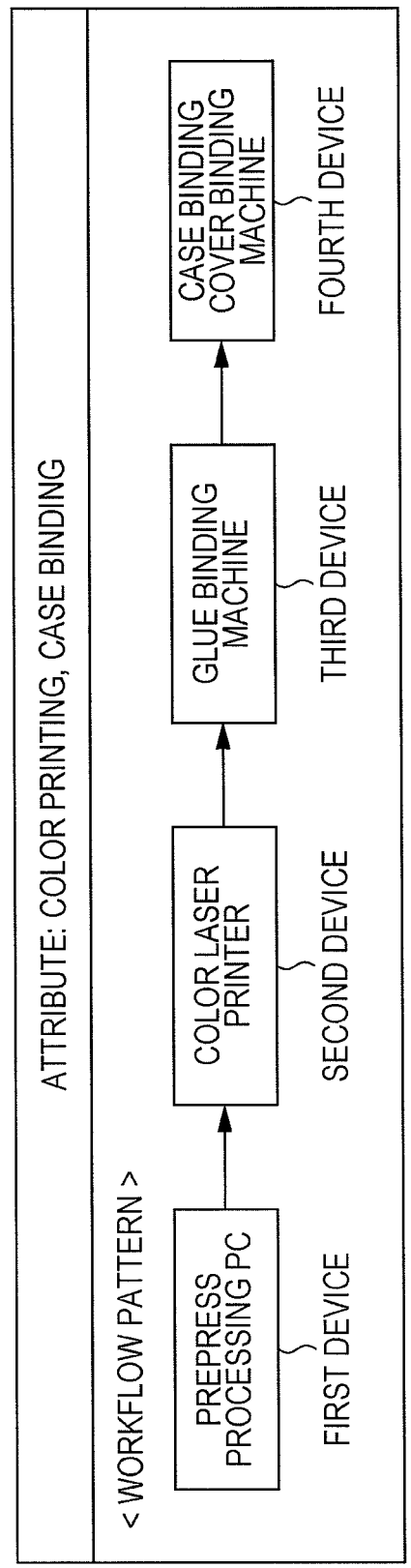
FIG. 2A is a diagram illustrating a schematic example of a workflow rule.
Figure 2B:
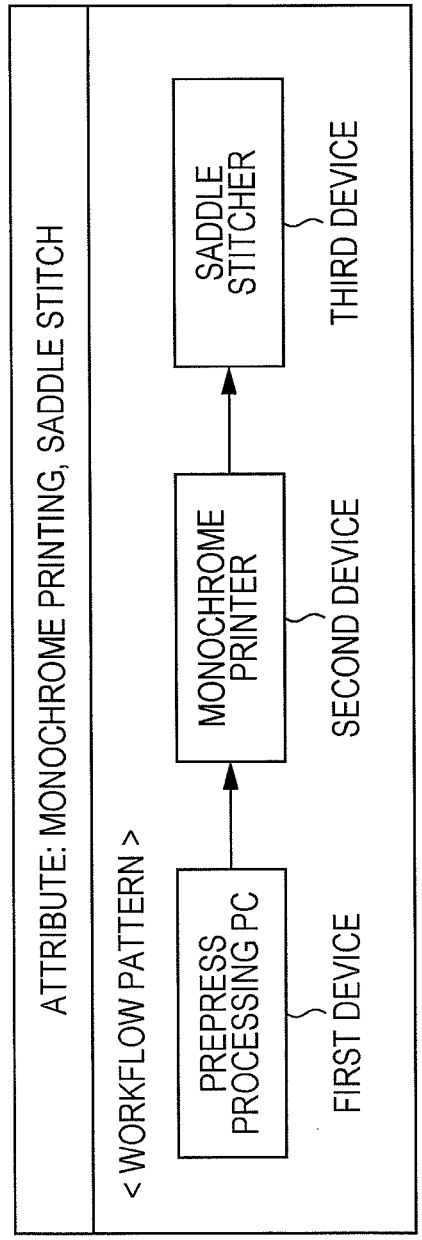
FIG. 2B is a diagram illustrating another schematic example of a workflow rule.

FIGS. 2A and 2B illustrate schematic examples of a workflow rule stored in the workflow rule storage unit 40. FIG. 2A illustrates an example of a rule for a workflow pattern corresponding to a print job of creating a booklet using color printing and case binding. FIG. 2B illustrates an example of a rule for a workflow pattern corresponding to a print job of creating a booklet using monochrome printing and saddle stitch. Referring to FIG. 2A, a workflow pattern indicating that processing operations are to be sequentially executed by four devices 30, i.e., a prepress processing PC, a color laser printer, a glue binding machine, and a case binding cover binding machine, is associated with a combination of attributes of a printed material "color printing" and "case binding". Referring to FIG. 2B, a workflow pattern indicating that processing operations are to be sequentially executed by three devices 30, i.e., a prepress processing PC, a monochrome printer, and a saddle stitcher, is associated with a combination of attributes of a printed material "monochrome printing" and "saddle stitch".

Upon obtaining attribute information including a combination of attributes "color printing" and "case binding" from a print job, for example, the workflow generator 208 reads out the workflow pattern illustrated in FIG. 2A from the workflow rule storage unit 40. Also, the workflow generator 208 specifies the correspondence between the devices included in the read out workflow pattern (prepress processing PC, color laser printer, glue binding machine, and case binding cover binding machine) and the devices 30 in the system, and generates a workflow by arranging the pieces of identification information of the devices 30 in the order indicated by the workflow pattern illustrated in FIG. 2A. The specification of the devices 30 in the system may be performed by referring to the identification information of the individual devices 30 and the types of the individual devices 30, which are stored in the device information storage unit 202.

The rule stored in the workflow rule storage unit 40 may not necessarily have the form illustrated in FIGS. 2A and 2B, as long as a workflow pattern may be specified in accordance with a combination of attributes of a printed material. For example, a combination of attributes associated with a workflow pattern may be described using a logical expression in which the value of the term of an attribute is an argument.

Referring back to FIG. 1, after generating a workflow corresponding to a print job, the workflow generator 208 specifies, regarding each of the devices 30 included in the generated workflow, the information to be used for calculating a time period from the start to the end of processing executed by the device 30 (hereinafter referred to as "processing period"). The information to be used for calculating the processing period of each device 30 is specified by using the attribute information obtained from a print job, and the information representing input to and output from each device 30 estimated to be performed during processing of the print job. For example, among pieces of the attribute information, the information related to the amount of processing executed by each device 30 in the workflow, such as the document size, the number of pages, and the number of copies of the printed material to be created, is specified as the information to be used for calculating the processing period of the device 30. The input to one of the devices 30 in the workflow relates to the amount of processing executed in the device 30, and the output from the device 30 corresponds to the input to the subsequent device 20 in the workflow. Thus, the output from a certain device 30 may relate to the amount of processing executed in the subsequent device 30. Therefore, the information representing input to and output from each device 30 may be specified as the information to be used for calculating the processing period of each device.

For example, the case of processing a print job for creating one or more booklets using duplex monochrome printing and saddle stitch will be discussed. In this example, the attribute information obtained from the print job includes a combination of attributes "monochrome printing" and "saddle stitch", and thus a workflow is generated in accordance with the workflow pattern illustrated in FIG. 2B. Also, the attribute information obtained from the print job includes, in addition to the attributes "monochrome printing" and "saddle stitch", an attribute representing "duplex printing", an attribute representing "no N-up setting", a document size, the number of pages of each booklet, and the number of booklets to be created. The prepress processing PC, which is the first device 30 in the generated workflow, receives page description language (PDL) data in which all the pages to be printed are described in PDL, and converts the received PDL data, thereby generating image data in the format suitable for being printed in the monochrome printer, which is the second device 30 in the workflow. In this example, the output from the prepress processing PC is image data of all the pages to be printed. Here, the processing period of the prepress processing PC depends on the document size and the number of pages to be processed. Thus, the document size and the number of pages included in the attribute information are specified as the information to be used for calculating the processing period of the prepress processing PC. The monochrome printer, which is the second device 30, receives the image data output from the prepress processing PC, and performs duplex printing based on the number of pages and the number of copies represented by the attribute information on sheets having the document size represented by the attribute information. In this example, the attribute information includes an attribute "no N-up setting", and thus the monochrome printer prints one page of data on one face (front face or back face) of a sheet. The monochrome printer outputs the above-described number of copies of printed sheets, on which duplex printing has been performed on the above-described number of pages of sheets having the above-described document size. The period for printing performed by the monochrome printer depends on whether or not duplex printing is performed, whether or not N-up setting is performed, the document size, the number of pages, and the number of copies. Thus, the attribute "duplex printing", the attribute "no N-up setting", the document size, the number of pages, and the number of copies included in the attribute information are specified as the information to be used for calculating the processing period of the monochrome printer. The saddle stitcher, which is the third device 30, receives the printed sheets output from the monochrome printer, and performs a binding process of binding the received sheets into booklets each having the number of pages specified by the attribute information and stapling the center of each booklet. The output from the saddle stitcher corresponds to saddle-stitched booklets the number of which is represented by the attribute information. The period for processing performed by the saddle stitcher depends on the number of booklets to be created, and thus the number of copies included in the attribute information is specified as the information to be used for calculating the processing period of the saddle stitcher.

The type of information to be specified as the information to be used for calculating the processing period for each type of device 30 may be described in, for example, a workflow pattern stored in the workflow rule storage unit 40. Alternatively, the type of information may be registered in the device information storage unit 202 in association with the identification information of the individual devices 30.

The activation period specifying unit 210 specifies the activation period of each of the devices 30 included in the workflow generated by the workflow generator 208. The activation period of each device 30 corresponds to the period of activation for switching the power state of the device 30 from the current power state to the idle mode. The activation period specifying unit 210 reads out the power state information and operation information of the individual devices 30 included in the workflow from the device information storage unit 202, and obtains the activation periods of the individual devices 30 using the read out power state information and operation information. For example, in a case where the current power state of a certain device 30 is the OFF state, a return period from the OFF state, which is included in the operation information of the device 30, is regarded as an activation period of the device 30. For example, in a case where the current power state of the device 30 is the power-saving mode, a return period from the power-saving mode may be regarded as an activation period.

The processing period calculator 212 calculates the processing periods of the individual devices 30 included in the workflow generated by the workflow generator 208. The processing period calculator 212 includes calculators corresponding to the individual devices 30 included in the system. For example, in the system including N devices 30 illustrated in FIG. 1, the processing period calculator 212 includes N calculators corresponding to the N devices 30: a first-device calculator 212-1; a second-device calculator 212-2; ...; and an N-th-device calculator 212-N. Each of these N calculators holds, in a storage device that is not illustrated, a procedure of calculating a processing period in accordance with the type and specifications of the corresponding device 30, and calculates the processing period of the corresponding device 30 in accordance with the procedure. The processing period calculator 212 specifies the calculators corresponding to the identification information of the devices 30 included in the workflow among the N calculators, and each of the specified calculators calculates the activation period and the processing period of the corresponding device 30.

The processing period of each of the devices 30 included in the workflow is calculated using the information specified by the workflow generator 208 as the information to be used for calculating the processing period of the device 30, and the operation information of the device 30. For example, the above-described example illustrated in FIG. 2B (the example of a print job of creating a booklet using duplex monochrome printing and saddle stitch) will be discussed. Regarding the prepress processing PC, which is the first device 30, the information representing the performance of the prepress processing PC is obtained from the operation information of the prepress processing PC, and the processing period is calculated using the obtained information representing the performance, and the document size and the number of pages of the printed material to be created. Regarding the monochrome printer, which is the second device 30, the values of PPM and FPOT in the case of performing duplex printing using the document size of the printed material to be created are obtained from the operation information of the monochrome printer, and the processing period is calculated using the obtained values of PPM and FPOT, and the number of pages and the number of copies of the printed material to be created. In this example, the number of pages is represented by Np and the number of copies is represented by Ns. Due to "no N-up setting", the product of the number of pages Np and the number of copies Ns corresponds to the number of faces of sheets on which printing is to be performed by the monochrome printer. Thus, the processing period of the monochrome printer may be calculated by using the following expression (1).

$$\text{FPOT} + (Np \times Ns - 1)/\text{PPM} \qquad (1)$$

In the case of "N-up setting", the number of faces of sheets on which printing is to be performed may be obtained from a result of dividing the number of pages Np by the number of pages per face, and the calculated number of faces may be used instead of "Np" in expression (1). Regarding the saddle stitcher, which is the third device, the processing period may be calculated by obtaining, from the operation information of the saddle stitcher, the number of booklets that may be created per unit time, and by dividing the number of copies of the printed material to be created by the obtained number of booklets.

The procedure of calculating a processing period varies depending on the type and specifications of each device 30, and is not limited to the above-described example. For example, the temperature and humidity inside the device 30 or near the device 30 may affect the processing period. In this case, the processing period calculator 212 calculates the processing period by obtaining not only operation information and attribute information but also the corresponding values of temperature and humidity. The values of temperature and humidity may be obtained from a sensor that is set in advance inside or near the device 30.

The activation starting time determining unit 214 determines the times when the activation operations of the individual devices 30 included in the workflow start, by using the activation periods specified by the activation period specifying unit 210 and the processing periods calculated by the processing period calculator 212. In the exemplary embodiment, the starting times of the activation operations of the individual devices 30 are determined so that the end time of an activation operation matches the starting time of processing of a print job in the first device, and that the end time of an activation operation matches the end time of a processing operation in the preceding device 30 in the subsequent devices. Here, the term "match" includes complete matching between two times, and also includes a case where the difference between two times is within a predetermined time range (for example, one to five seconds).

FIG. 3 illustrates an example of execution timings of activation operations and processing operations of the individual devices 30 in a case where a print job is processed by sequentially using devices 30, the number of which is K, and where the activation starting time determining unit 214 according to the exemplary embodiment determines the starting times of the activation operations of the individual devices 30. In the description given below, the activation period of the i-th device 30 (i=1, 2, . . . , and K) is represented by $I_i$, and the processing period thereof is represented by $D_i$. Referring to FIG. 3, when it is assumed that the starting time of processing of a print job, that is, the starting time of the processing operation executed by the first device 30, is represented by $T_{job}$, the activation starting time determining unit 214 determines to start the activation operation of the first device 30 at time $T_{job}-I_1$, which is earlier than time $T_{job}$ by the activation period $I_1$ of the first device 30. In this case, the end time of the processing operation of the first device 30 is time $T_{job}+D_1$, which is later than time $T_{job}$, at which the processing operation starts, by a processing period $D_1$ of the first device 30. The activation starting time determining unit 214 determines to start the activation operation of the second device 30 at time $T_{job}+D_1-I_2$, which is earlier than time $T_{job}+D_1$ by an activation period $I_2$ of the second device 30, so that the processing operation of the second device 30 may be started at time $T_{job}+D_1$. Likewise, the activation starting time determining unit 214 determines the starting time of the activation operation of each of the third to K-th devices 30. As a result of determining the starting times of the activation operations of the first to K-th devices 30 in the above-described manner, the end time of the processing operation of a certain device 30 matches the starting time of the processing operation of the subsequent device 30, as illustrated in FIG. 3.

In the example illustrated in FIG. 3, the first to K-th devices 30 switch their power state to the power-saving mode or the OFF state after the respective processing operations end. Accordingly, in the example illustrated in FIG. 3, the individual devices 30 do not consume power in the idle mode.

FIG. 4 illustrates the activation starting times and the processing end times of the individual devices 30 in a case where the activation starting times of the first to K-th devices 30 are determined in the manner described above with reference to FIG. 3. In the table illustrated in FIG. 4, the device numbers 1, 2, 3, . . . , K−1, and K correspond to the first to K-th devices 30 illustrated in FIG. 3, respectively. The activation starting time of the first device 30 (having the device number "1") is time $T_{job}-I_1$, which is earlier than the starting time $T_{job}$ of the printing job by the activation period $I_1$ of the first device 30, as described above. The activation starting time of each of the second to K-th devices 30 is a time earlier than the processing end time of the preceding device 30 by the activation period of the device 30. In this example, the processing operation of a certain device 30 starts at the time when the processing operation of the preceding device 30 ends. Thus, the processing end time of each device 30 is represented by a value obtained by adding the starting time $T_{job}$ of the print job and the sum of the processing periods of the first device to the corresponding device.

In the example described above with reference to FIGS. 3 and 4, the activation starting time determining unit 214 determines, as a starting time of the activation operation of each device 30, a relative time with respect to the starting time $T_{job}$ of a print job. The activation starting time determining unit 214 supplies the information representing the determined times to the scheduler 216. For example, the activation starting time determining unit 214 may supply, to the scheduler 216, the expressions that express the activation starting times of the individual devices 30 shown in the column "activation starting time" in the table illustrated in FIG. 4.

Referring back to FIG. 1, the scheduler 216 creates a schedule of control for causing the individual devices 30 to start activation operations at the times determined by the activation starting time determining unit 214. The schedule created by the scheduler 216 may describe which control signal is to be transmitted to which device at which time, for example. The scheduler 216 according to the exemplary embodiment receives, from the activation starting time determining unit 214, the expressions that express the activation starting times of the individual devices 30 illustrated in FIG. 4, and converts the received expressions into values representing the actual times. For example, the scheduler 216 sets, as the value representing the activation starting time $T_{job}-I_1$ of the first device 30, a time later than the time when the expressions that express the activation starting times of the individual devices 30 are received from the activation starting time determining unit 214. At this time, if the value representing the time just after the current time is set as $T_{job}-I_1$, the activation operation of the first device 30 starts just after the scheduler 216 has received the expressions that express the activation starting times. The activation period $I_1$ of the first device 30 has been specified by the activation period specifying unit 210, and thus the starting time $T_{job}$ of the processing of the print job is determined by setting the value of $T_{job}-I_1$. The scheduler 216 obtains the values of the activation starting times of the second to K-th devices 30 by performing calculation by substituting the value of a processing starting time $T_{job}$ of the print job, the value of the activation period $I_i$ of each device 30 specified by the activation period specifying unit 210, and the value of the processing period $D_i$ of each device 30 calculated by the processing period calculator 212 into each of the expressions that express the activation starting times of the second to the K-th devices 30. The scheduler 216 generates a schedule of transmitting a print job and a schedule of transmitting activation start instructions by using the values of the activation starting times of the first to K-th devices 30 and the value of the processing starting time $T_{job}$ of the print job. An example of the generated schedules is illustrated in FIGS. 5 and 6.

FIG. 5 illustrates an example of the schedule of transmitting a print job to the first device 30. The table in FIG. 5 includes an ID, a job transmission time $T_{job}$, the name of a destination device, and the IP address of the destination device. The ID is identification information of a process of transmitting a single control signal from the print server 20 to a device 30 in association with the processing of the print job. The scheduler 216 assigns a single ID to single transmission of a control signal. In the table in FIG. 5, the job transmission time $T_{job}$ represents the above-described processing starting time $T_{job}$ of the print job. The name of a destination device represents the name assigned to the first device 30. The IP address of the destination device represents the IP address of the first device 30. Regarding the name and IP address of the destination device, the names and IP addresses of the individual devices 30 may be registered in the device information storage unit 202 in association with the identification information of the devices 30, and the name and IP address associated with the identification information of the first device 30 may be read out and may be included in the schedule.

FIG. 6 illustrates an example of the schedule of transmitting activation start instructions to the individual devices 30. The table in FIG. 6 includes IDs, activation start instruction transmission times, the names of target devices, and the IP addresses of the target devices. Each row in the table in FIG. 6 corresponds to a schedule of transmitting an activation start instruction to a single device 30. FIG. 6 illustrates an example of a case where four devices 30 are included in a workflow (K=4). In the table in FIG. 6, an ID represents the identification information of a process of transmitting a control signal, like the ID in the table in FIG. 5. An ID having a smaller value is assigned to a process of transmitting a control signal to the device 30 having an earlier order in a workflow. The activation start instruction transmission time represents the time to transmit a control signal representing an instruction to start an activation operation to the corresponding device 30, and is the value of the activation starting time obtained for each device 30 in the above-described manner. The name and IP address of the target device represent the name and IP address of the corresponding device 30. The name and IP address of the target device may be obtained from the device information storage unit 202, like the name and IP address of the destination device illustrated in FIG. 5.

Referring back to FIG. 1, the scheduler 216 supplies the schedule of transmitting a print job to the job transmitter 218 and supplies the schedule of transmitting activation start instructions to the activation controller 220.

The job transmitter 218 transmits a print job in accordance with the schedule created by the scheduler 216. For example, in the case of the schedule shown in the table in FIG. 5, the job transmitter 218 transmits the print job to the IP address "192.10.22.101" of the prepress processing PC, which is the first device 30, at the time "9:47:42". The device 30 that has received the print job executes the processing operation assigned thereto in accordance with the received print job. Also, the job transmitter 218 according to the exemplary embodiment transmits the information about the workflow generated by the workflow generator 208 to the first device 30, together with the print job. The first device 30 obtains the identification information of the subsequent device 30 (second device) with reference to the information about the workflow, and supplies a result of the processing operation executed by the first device 30 and the information about the workflow to the second device 30. Each of the second device 30 and the subsequent devices 30 specifies the subsequent device 30 with reference to the information about the workflow, and supplies a result of the processing operation executed thereby and the information about the workflow to the specified device 30.

The activation controller 220 controls the individual device 30 so that the individual devices 30 start an activation operation in accordance with the schedule created by the scheduler 216. For example, in the case of the schedule shown in the table in FIG. 6, the activation controller 220 transmits a control signal representing an instruction to start an activation operation to each of the IP addresses of the prepress processing PC, color laser printer, glue binding machine, and case binding cover binding machine at the times indicated by the activation start instruction transmission times.

The power state controller 34 of each device 30 that has received the control signal from the activation controller 220 executes an activation operation of switching the power state to the idle mode. In the exemplary embodiment, at the time when the activation operation of a certain device 30 ends and the certain device 30 enters the idle mode, the processing operation of the preceding device 30 ends, and the processing result is supplied to the certain device 30. Thus, each device 30 starts the processing operation assigned thereto at the same time when the activation operation ends, and the power state is switched from the idle mode to the processing execution mode.

Figure 7:
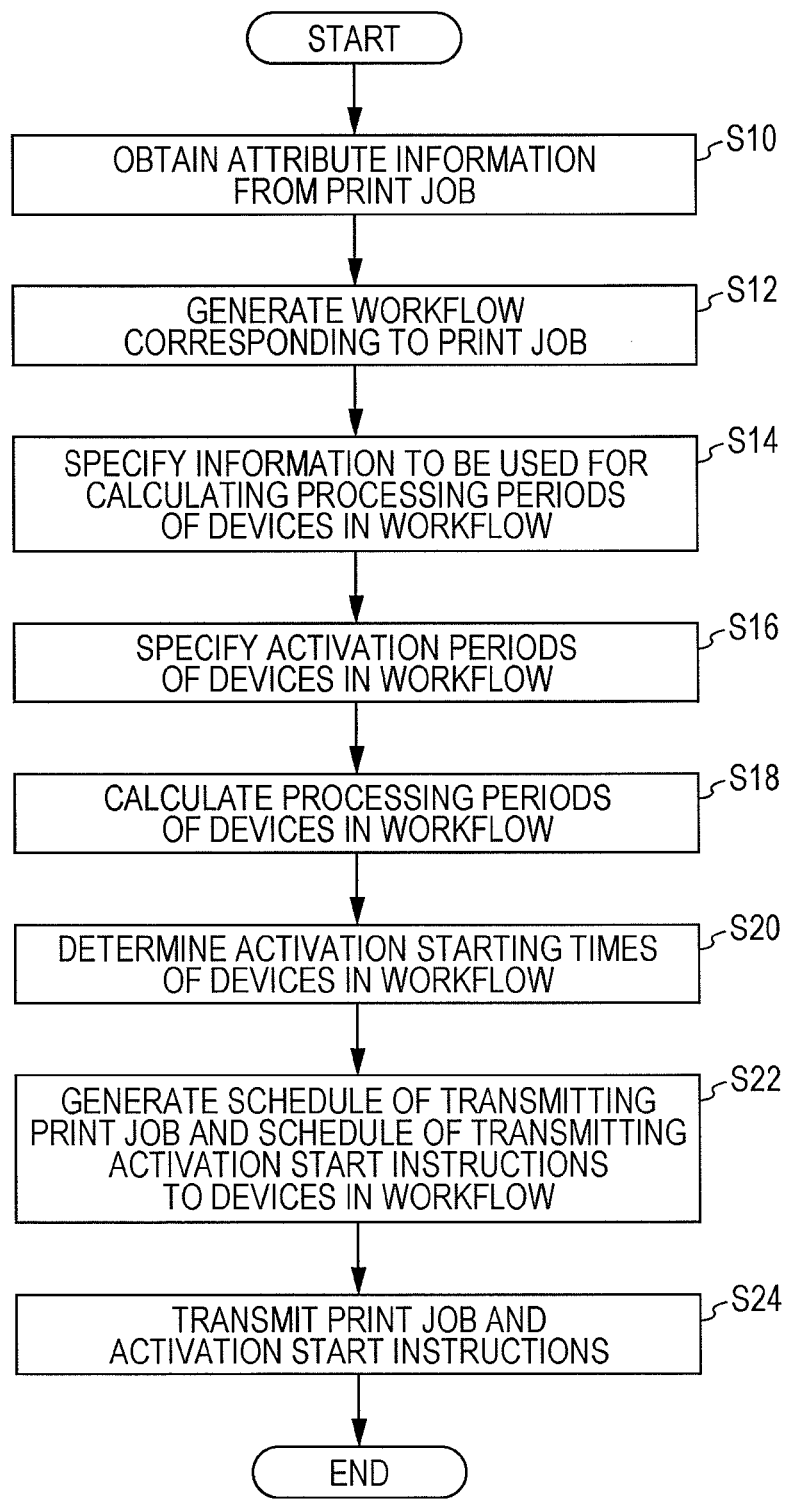
FIG. 7 is a flowchart illustrating an example of a procedure of a process performed by a print server.

Hereinafter, an example of the procedure of a process performed by the print server 20 will be described with reference to FIG. 7. The print server 20 starts the process illustrated in FIG. 7 upon receiving a print job from the client 10.

The job receiver 204 of the print server 20 supplies the print job received from the client 10 to the job attribute information obtaining unit 206. The job attribute information obtaining unit 206 obtains attribute information from the received print job (step S10). The attribute information represents the attributes of the printed material to be created in accordance with the received print job, and includes attributes, such as a document size, which of simplex and duplex printing is to be performed, which of monochrome and color printing is to be performed, whether or not N-up setting is performed, the number of pages, the number of copies, and a finishing scheme.

Subsequently, the workflow generator 208 generates a workflow corresponding to the print job to be processed, by using the attribute information obtained by the job attribute information obtaining unit 206 in step S10 (step S12). For example, the workflow generator 208 specifies a workflow pattern corresponding to a combination of the attributes included in the attribute information obtained in step S10, with reference to the content of the workflow rule storage unit 40 (see FIGS. 2A and 2B). Then, the workflow generator 208 reads out, from the device information storage unit 202, the identification information of the devices 30 corresponding to the types of individual devices included in the specified workflow pattern. Furthermore, the workflow generator 208 generates a workflow indicating that processing operations are to be executed by the respective devices 30 identified by the readout identification information in the order indicated by the workflow pattern. The workflow generator 208 supplies the workflow generated in step S12 to the activation period specifying unit 210 and the processing period calculator 212.

After generating the workflow, the workflow generator 208 specifies the information to be used for calculating the processing periods of the individual devices 30 included in the generated workflow (step S14). For example, as in the specific example described above with reference to FIG. 2B, the information related to the amount of processing executed by the individual devices 30, among the attribute information obtained from the print job and the information related to input to and output from the individual devices 30 included in the workflow, is specified as the information to be for calculating the processing periods. The workflow generator 208 supplies the information specified in step S14 to the processing period calculator 212.

Subsequently, the activation period specifying unit 210 specifies the activation periods of the individual devices 30 in the workflow (step S16). For example, the activation period specifying unit 210 reads out, from the device information storage unit 202, the power state information and operation information associated with the identification information of the individual devices 30 included in the workflow generated in step S12. Then, the activation period specifying unit 210 specifies, for each of the devices 30, a return period from the current power state indicated by the power state information to the idle mode, the return period being included in the operation information and specified as the activation period of the device 30. The activation period specifying unit 210 supplies the activation periods specified for the individual devices 30 to the activation starting time determining unit 214.

The processing period calculator 212 calculates the processing periods of the individual devices 30 in the workflow (step S18). For example, the processing period calculator 212 specifies the calculators to be used among the calculators for the N devices 30, by using the identification information of the devices 30 included in the workflow generated in step S12. Then, each of the specified calculators calculates the processing period of the corresponding device 30 by using the information specified in step S14 as the information to be used for calculating the processing period of the device 30. The processing period calculator 212 supplies the processing periods calculated for the individual devices 30 to the activation starting time determining unit 214.

The process of specifying the activation periods (step S16) and the process of calculating the processing periods (step S18) may be performed in parallel, or the order of executing the processes may be reversed.

The activation starting time determining unit 214 determines the times when the activation operations are to be started in the individual devices 30 in the workflow (step S20). In the exemplary embodiment, in step S20, the activation starting time determining unit 214 determines the activation starting times of the individual devices 30 so that the end time of the activation operation of the first device in the workflow matches the processing starting time of the print job, and that the end time of the activation operation matches the end time of the processing operation in the preceding device 30 in the subsequent devices 30. The activation starting times of the individual devices 30 described above with reference to FIGS. 3 and 4 correspond to a specific example of the activation starting times determined in step S20. The activation starting time determining unit 214 supplies, to the scheduler 216, the activation starting times of the individual devices 30 determined in step S20.

The scheduler 216 generates a schedule of transmitting the print job and a schedule of transmitting activation start instructions to the individual devices 30 in the workflow, in accordance with the activation starting times of the individual devices 30 determined in step S20 (step S22). For example, the scheduler 216 determines the values of specific times of transmitting the print job and transmitting the activation start instructions in accordance with the activation starting times of the individual devices 30, each of the activation starting times being obtained as a relative time with respect to the processing starting time of the print job. The schedules described above with reference to FIGS. 5 and 6 correspond to specific examples of the schedules generated by the scheduler 216 in step S22. The scheduler 216 supplies the schedule of transmitting the print job to the job transmitter 218, and supplies the schedule of transmitting the activation start instructions to the activation controller 220.

The job transmitter 218 and the activation controller 220 transmit the print job and the activation start instructions, respectively, in accordance with the schedules generated by the scheduler 216 in step S22 (step S24). For example, the activation controller 220 transmits, to each of the devices 30 in the workflow, a control signal representing an instruction to start an activation operation of the device 30 at the time indicated by the schedule of transmitting the activation start instructions.

According to the exemplary embodiment described above, the end time of the processing operation of a certain device 30 matches the end time of the activation operation of the subsequent device 30. Thus, the subsequent device 30 starts the processing operation assigned thereto without a waiting time in the idle mode, after the processing operation of the certain device 30 ends.

Figure 8:
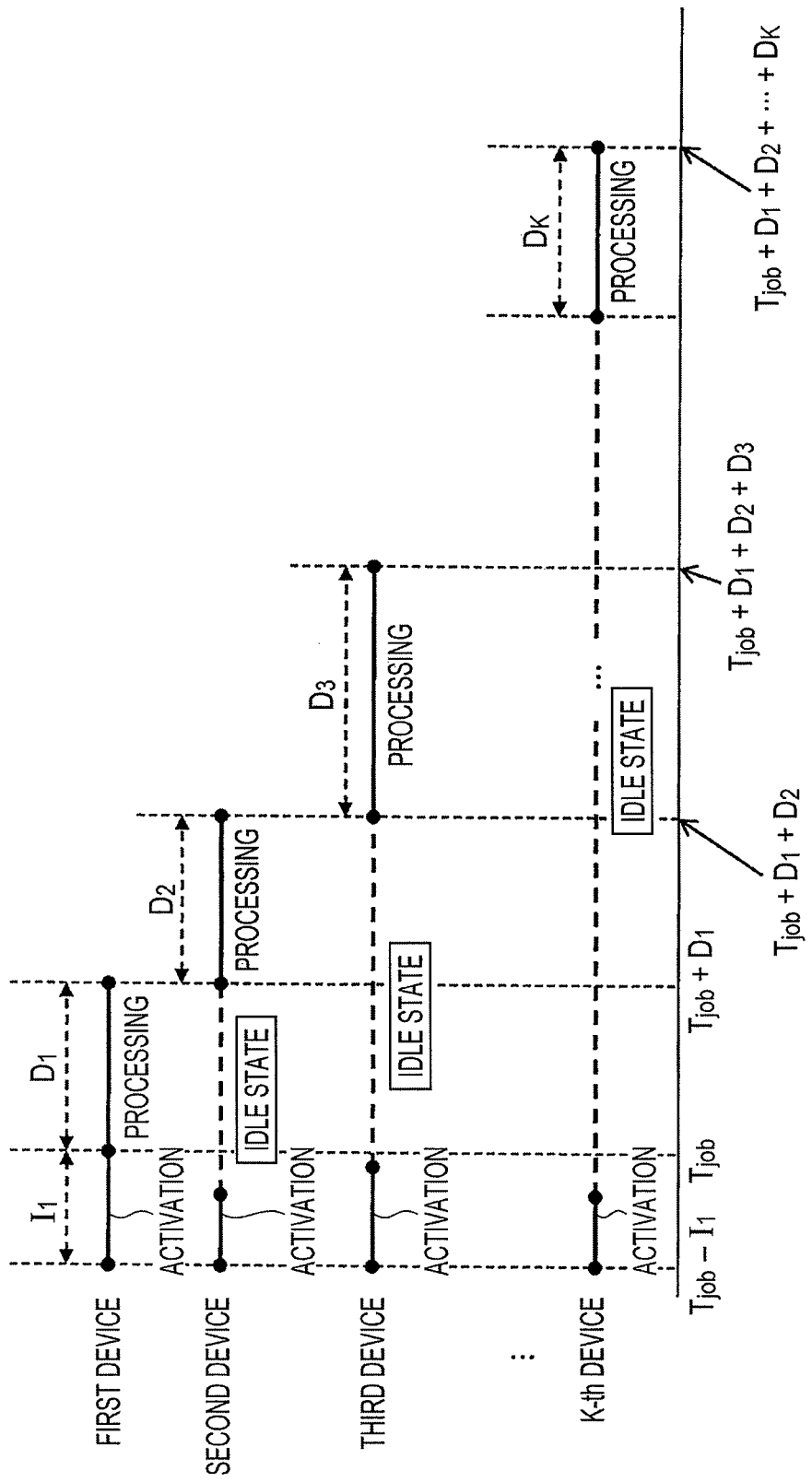
FIG. 8 is a diagram illustrating an example of processing operations executed by individual devices in time series in the case of starting activation operations of the individual devices at timings different from those in the exemplary embodiment.
Figure 9:
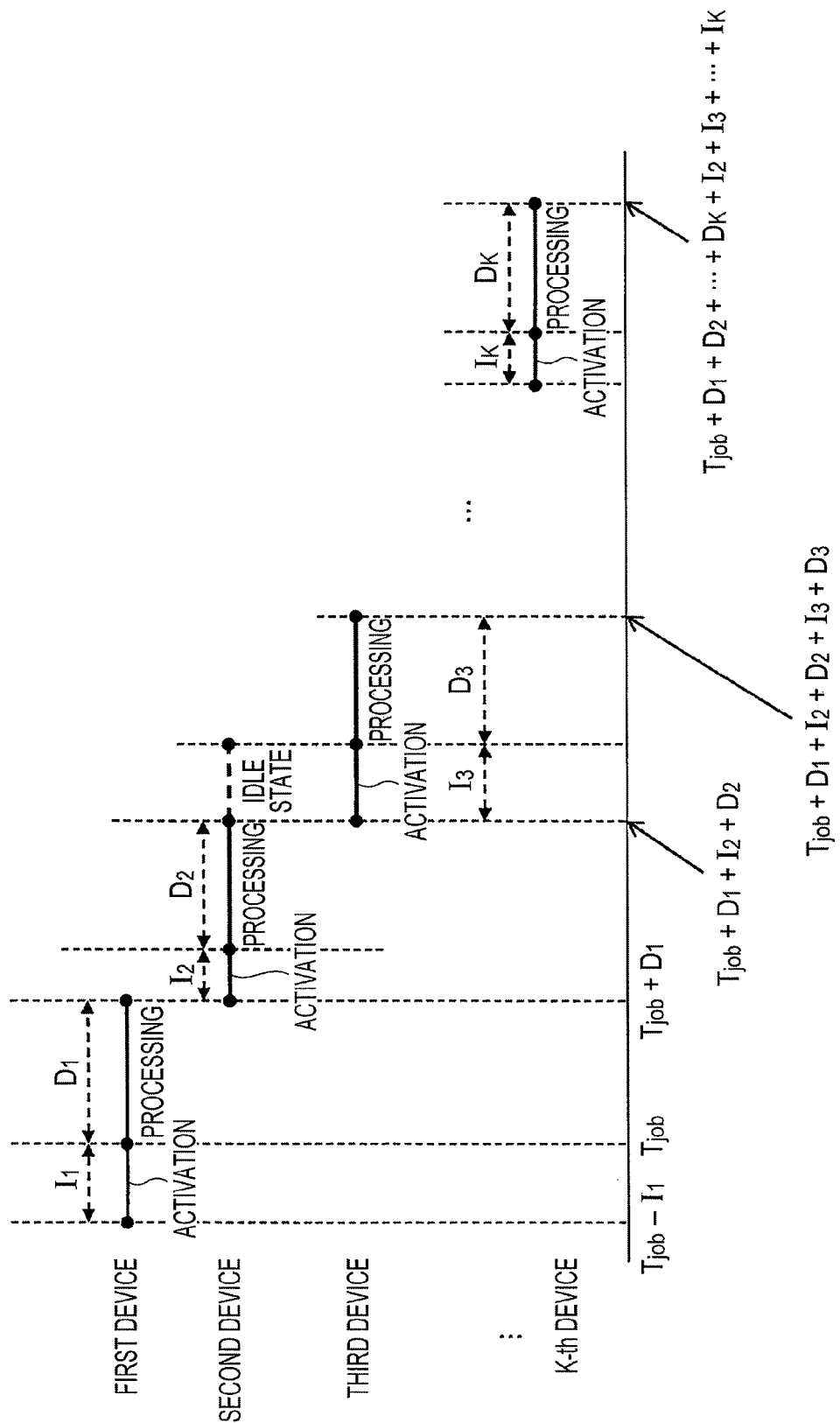
FIG. 9 is a diagram illustrating another example of processing operations executed by individual devices in time series in the case of starting activation operations of the individual devices at timings different from those in the exemplary embodiment.

Hereinafter, with reference to FIGS. 8 and 9, description will be given of an example of processing operations executed by the individual devices 30 in a case where activation operations of the individual devices 30 in a workflow are started at the timings different from those in the above-described exemplary embodiment. FIG. 8 illustrates an example of the case of starting the activation operations of all the devices 30 in the workflow before starting the processing of a print job. FIG. 9 illustrates an example of the case of starting the activation operation of each of the second to K-th devices 30 at the time when the processing operation of the preceding device 30 ends. In both the examples illustrated in FIGS. 8 and 9, a print job is processed by the first to K-th devices 30, as in the above-described example of the processing operations executed by the individual devices 30 illustrated in FIG. 3. In both the examples illustrated in FIGS. 8 and 9, the processing starting time of the print job is $T_{job}$, as in the example illustrated in FIG. 3. In FIGS. 8 and 9, the activation period of a device i (i=1, 2, . . . , and K) is represented by $I_i$, and the processing period thereof is represented by $D_i$.

In the example illustrated in FIG. 8, all the first to K-th devices 30 are caused to start respective activation operations at the same time $T_{job}-I_1$. The first device 30 starts the processing of the print job at the end time of the activation operation (time $T_{job}=T_{job}-I_1+I_1$). Each of the second to K-th devices 30 waits in the idle state, after the activation operation ends, until the processing operation of the preceding device 30 ends. After the processing operation of the preceding device 30 ends, the device 30 starts the processing operation assigned thereto. In the example illustrated in FIG. 8, the time when the processing of the print job ends, that is, the time when the processing operation of the K-th device 30 ends, is represented by $T_{job}+D_1+D_2+ \ldots +D_K$, as in the example illustrated in FIG. 3. In the example illustrated in FIG. 8, a larger amount of power is consumed than in the example illustrated in FIG. 3 by the amount of power consumed in the idle state from when the activation operation ends in the second to K-th devices 30 to when the processing operation starts in each of the second to K-th devices 30.

In the example illustrated n FIG. 9, the first device 30 is caused to start an activation operation at time $T_{job}-I_1$. Each of the second to K-th devices 30 is caused to start an activation operation when the processing operation of the preceding device 30 ends. According to the example illustrated in FIG. 9, unlike in the example illustrated in FIG. 8, the second to K-th devices 30 do not wait in the idle state from the end of the activation operation to the start of the processing operation. Accordingly, in the example illustrated in FIG. 9, the power consumption reduces compared to the example illustrated in FIG. 8. However, in the example illustrated in FIG. 9, the time when the processing of the print job ends is the time represented by $T_{job}+D_1+D_2+ \ldots +D_K+I_1+I_2+ \ldots +I_K$, which is obtained by adding the processing starting time $T_{job}$ of the print job, the sum of the processing periods of the individual devices 30, and the sum of the activation periods of the individual deices 30. In this case, the entire processing period of the print job is longer than in the example illustrated in FIG. 8. In the example illustrated in FIG. 3 according to the exemplary embodiment, the processing of the print job ends at the time $T_{job}+D_1+D_2+ \ldots +D_K$, as in the example illustrated in FIG. 8. Thus, according to the example illustrated in FIG. 9, the entire processing period of the print job is longer than in the example illustrated in FIG. 3. Furthermore, in the example illustrated in FIG. 9, in a case where a certain device 30 may receive a result of the processing operation of the preceding device 30 after the certain device 30 has ended the activation operation, an idle state occurs after the processing operation ends in the preceding device 30, that is, a waiting period of waiting for the end of the activation operation of the subsequent device is generated. As an example of such a case, FIG. 9 illustrates an "idle state" that continues from the end of the processing operation of the second device 30 to the end of the activation operation of the third device 30. The power consumption in such an idle state does not occur in the example illustrated in FIG. 3 according to the above-described exemplary embodiment.

As described above with reference to FIGS. 8 and 9, in the above-described exemplary embodiment in which the activation operations of the individual devices 30 are started so that the end time of the activation operation of each device 30 matches the end time of the processing operation of the preceding device 30, a print job is processed with lower power consumption than in a case where the activation operations of all the devices 30 are started before starting the processing of the print job and a case where the activation operation of each of the second to K-th devices 30 is started at the time when the processing operation of the preceding device 30 ends. Also, in the above-described exemplary embodiment, the time period over which processing of the print job is performed corresponds to the sum of the processing periods of the individual devices 30. That is, the print job is processed in a shorter time period than in a case where the activation operation of each of the second to K-th devices 30 is started at the time when the processing operation of the preceding device 30 ends.

In the above-described exemplary embodiment, a workflow is generated for each print job, and an activation start instruction is transmitted to each of the devices 30 included in the workflow. Therefore, in the above-described exemplary embodiment, the activation control of the individual devices 30 corresponding to each print job is performed. Furthermore, in the above-described exemplary embodiment, each device 30 is in the power-saving mode or in the OFF state when not executing a processing operation. Thus, in the above-described exemplary embodiment, the devices 30 are in the power-saving mode or in the OFF state when not executing a processing operation of the print job that is being processed or when not executing an activation operation for the subsequent processing operation.

The above-described exemplary embodiment is simply an example of the embodiment of the present invention, and various modifications are applicable in addition to the above-described exemplary embodiment. For example, in the above-described exemplary embodiment, the power state controller 34 of each device 30 sets the power state of the device 30 to the power-saving mode or the OFF state after the processing execution unit 32 has ended a processing operation. According to a modification, instead of setting the power state to the power-saving mode or the OFF state by the device 30 itself after the processing operation has ended, the power state of each device 30 may be set to the power-saving mode or the OFF state in accordance with a control signal supplied from the print server 20. For example, at the end time of the processing operation of each device 30, the print server 20 may transmit, to the device 30, a control signal representing an instruction to switch the power state to the power-saving mode or the OFF state, and the power state controller 34 of the device 30 that has received the control signal may set the power state of the device 30 to the power-saving mode or the OFF state in accordance with the control signal.

According to another modification, each device 30 may not necessarily set the power state to the power-saving mode or the OFF state at the end of the processing operation. For example, the power state controller 34 of each device 30 may set the power state to the idle mode at the end of the processing operation.

Figure 10:
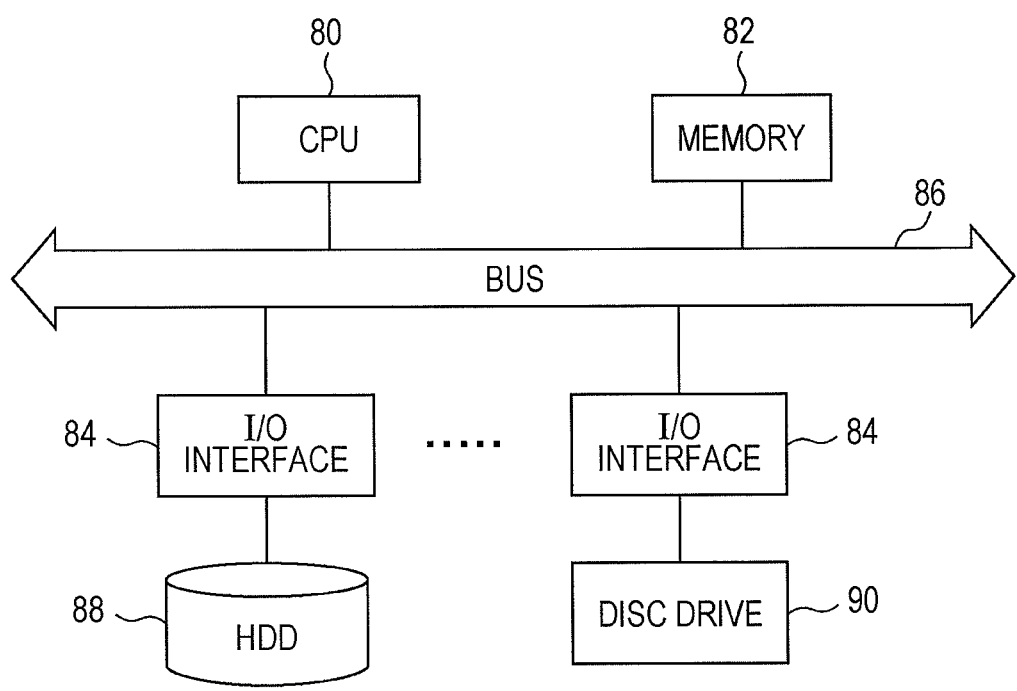
FIG. 10 is a diagram illustrating a hardware configuration of a computer.

Typically, the above-described print server 20 is realized by executing, with a multi-purpose computer, a program describing the functions of the individual units of the print server 20 or the details of processing performed by the print server 20. As illustrated in FIG. 10, the computer has a circuit configuration that includes, as hardware units, a central processing unit (CPU) 80, a memory (first storage) 82, and various input/output (I/O) interfaces 84, which are connected to one another via a bus 86. Also, a hard disk drive (HDD) 88 and a disc drive 90 are connected to the bus 86 via the I/O interfaces 84, for example. The disc drive 90 is used to read data stored in portable nonvolatile recording media of various standards, such as a compact disc (CD), a digital versatile disc (DVD), and a flash memory. The HDD 88 or the disc drive 90 functions as an external storage device with respect to the memory 82. The program describing the processing according to the exemplary embodiment is stored in a fixed storage device, such as the HDD 88, via a recording medium such as a CD or DVD, or via a network, and is installed to the computer. The processing according to the exemplary embodiment is realized when the program stored in the fixed storage device is read out to the memory 82 and is executed by the CPU 80.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A control device comprising:
a generating unit that generates, upon receiving a print instruction, which includes attribute information representing an attribute of a printed material to be created, from a terminal device, processing information by using the attribute information included in the print instruction and a rule that is preset regarding the attribute of the printed material and a plurality of processing operations to be executed for creating the printed material having the attribute, the processing information indicating which processing operations are to be executed in which order by which processing devices among a plurality of processing devices that execute different processing operations for creating the printed material, so as to create the printed material to be created;
a specifying unit that specifies activation periods of activation operations of activating respective processing devices indicated by the processing information, the activation periods being specified using operation information of the respective processing devices and power state information of the respective processing devices, the operation information and the power state information being obtained from the respective processing devices indicated by the processing information;

a calculating unit that calculates processing periods of the processing operations executed to create the printed material by the respective processing devices indicated by the processing information, the processing periods being calculated using the operation information, the power state information, and the attribute information included in the print instruction;

a determining unit that determines starting times of the activation operations executed by the respective processing devices indicated by the processing information by using the activation periods, the processing periods, and the order of the processing operations executed by the processing devices indicated by the processing information, so that an end time of a processing operation executed by a certain processing device among the processing devices matches an end time of an activation operation executed by a next processing device among the processing devices, the next processing device executing a processing operation subsequent to the certain processing device; and a controller that controls the respective processing devices indicated by the processing information so that the processing devices start respective activation operations at the starting times determined by the determining unit.

2. The control device according to claim 1, further comprising:

a transmitting unit that transmits the print instruction to a first processing device, which executes a processing operation first among the processing devices indicated by the processing information, at an end time of an activation operation executed by the first processing device.

3. The control device according to claim 1, wherein the controller further controls the respective processing devices indicated by the processing information so that power states of the processing devices are set to a power-saving mode or a power-off state at a time when the processing operations in the respective processing devices end.

4. The control device according to claim 2, wherein the controller further controls the respective processing devices indicated by the processing information so that power states of the processing devices are set to a power-saving mode or a power-off state at a time when the processing operations in the respective processing devices end.

5. A non-transitory computer readable medium storing a program causing a computer to execute a process, the process comprising:

generating, upon receiving a print instruction, which includes attribute information representing an attribute of a printed material to be created, from a terminal device, processing information by using the attribute information included in the print instruction and a rule that is preset regarding the attribute of the printed material and a plurality of processing operations to be executed for creating the printed material having the attribute, the processing information indicating which processing operations are to be executed in which order by which processing devices among a plurality of processing devices that execute different processing operations for creating the printed material, so as to create the printed material to be created;

specifying activation periods of activation operations of activating respective processing devices indicated by the processing information, the activation periods being specified using operation information of the respective processing devices and power state information of the respective processing devices, the operation information and the power state information being obtained from the respective processing devices indicated by the processing information;

calculating processing periods of the processing operations executed to create the printed material by the respective processing devices indicated by the processing information, the processing periods being calculated using the operation information, the power state information, and the attribute information included in the print instruction;

determining starting times of the activation operations executed by the respective processing devices indicated by the processing information by using the activation periods, the processing periods, and the order of the processing operations executed by the processing devices indicated by the processing information, so that an end time of a processing operation executed by a certain processing device among the processing devices matches an end time of an activation operation executed by a next processing device among the processing devices, the next processing device executing a processing operation subsequent to the certain processing device; and controlling the respective processing devices indicated by the processing information so that the processing devices start respective activation operations at the starting times determined in the determining.

6. A printing system comprising:

a plurality of processing devices that execute different processing operations for creating a printed material; and a control device that controls the plurality of processing devices, wherein the control device includes a generating unit that generates, upon receiving a print instruction, which includes attribute information representing an attribute of the printed material to be created, from a terminal device, processing information by using the attribute information included in the print instruction and a rule that is preset regarding the attribute of the printed material and a plurality of processing operations to be executed for creating the printed material having the attribute, the processing information indicating which processing operations are to be executed in which order by which processing devices among the plurality of processing devices, so as to create the printed material to be created, a specifying unit that specifies activation periods of activation operations of activating respective processing devices indicated by the processing information, the activation periods being specified using operation information of the respective processing devices and power state information of the respective processing devices, the operation information and the power state information being obtained from the respective processing devices indicated by the processing information, a calculating unit that calculates processing periods of the processing operations executed to create the printed material by the respective processing devices indicated by the processing information, the processing periods being calculated using the operation information, the power state information, and the attribute information included in the print instruction, a determining unit that determines starting times of the activation operations executed by the respective processing devices indicated by the processing information by using the activation periods, the processing periods, and the order of the processing operations executed by the processing devices indicated by the processing information, so that an end time of a processing operation executed by a certain processing device among the processing devices matches an end time of an activation operation executed by a next processing device among the processing devices, the next processing device executing a processing operation subsequent to the certain processing device, and a controller that controls the respective processing devices indicated by the processing information so that the processing devices start respective activation operations at the starting times determined by the determining unit.

* * * * *